（12）United States Patent
Webler et al.

(10) Patent No.: US 7,867,169 B2
(45) Date of Patent: Jan. 11, 2011

(54) ECHOGENIC NEEDLE CATHETER CONFIGURED TO PRODUCE AN IMPROVED ULTRASOUND IMAGE

(75) Inventors: William E. Webler, Escondido, CA (US); Mina Chow, Campbell, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 145 days.

(21) Appl. No.: 11/293,420

(22) Filed: Dec. 2, 2005

(65) Prior Publication Data

US 2007/0167822 A1 Jul. 19, 2007

(51) Int. Cl.
*A61B 8/14* (2006.01)
(52) U.S. Cl. .................. 600/463; 600/459
(58) Field of Classification Search .......... 600/459, 600/461–464, 466, 467, 479, 486
See application file for complete search history.

(56) References Cited

U.S. PATENT DOCUMENTS

| | | | | | |
|---|---|---|---|---|---|
| 3,984,911 | A | * | 10/1976 | Krug et al. | 29/424 |
| 4,052,989 | A | * | 10/1977 | Kline | 604/170.01 |
| 4,175,266 | A | * | 11/1979 | Nakano et al. | 347/77 |
| 4,234,887 | A | * | 11/1980 | Vanderslice, Jr. | 257/244 |
| 4,465,072 | A | | 8/1984 | Taheri | |
| 4,509,523 | A | * | 4/1985 | Pevsner | 600/435 |
| 4,960,134 | A | | 10/1990 | Webster, Jr. | |
| 5,045,072 | A | * | 9/1991 | Castillo et al. | 604/529 |
| 5,237,996 | A | | 8/1993 | Waldman et al. | |
| 5,242,429 | A | | 9/1993 | Nwaneri et al. | 604/270 |
| 5,275,162 | A | * | 1/1994 | Edwards et al. | 600/374 |
| 5,286,413 | A | | 2/1994 | Hannecart et al. | |
| 5,322,520 | A | | 6/1994 | Milder | |
| 5,411,527 | A | | 5/1995 | Alt | |
| 5,431,168 | A | | 7/1995 | Webster, Jr. | |
| 5,471,988 | A | | 12/1995 | Fujio et al. | |

(Continued)

FOREIGN PATENT DOCUMENTS

WO WO 97/19645 6/1997

(Continued)

OTHER PUBLICATIONS

Kimura et al, Distortion of Intravascular Ultrasound Images Because of Nonuniform Angular Velocity of Mechanical-Type Transducers, 1996, American Heart Journal, vol. 132 No. 2 part 1, p. 328-336.*

(Continued)

*Primary Examiner*—Long V Le
*Assistant Examiner*—Saurel J Selkin
(74) *Attorney, Agent, or Firm*—Blakely, Sokoloff, Taylor & Zafman LLP (57) ABSTRACT

An echogenic medical device, such as a needle catheter, which produces an improved ultrasonic image of the device, and a method of performing a medical procedure using a device of the invention. One aspect is directed to a catheter which reduces artifacts in the ultrasound image of the catheter. In one embodiment, the catheter has a spherical distal tip. Another aspect of the invention is directed to an echogenic catheter with echogenic portions arranged in an array to facilitate determination by ultrasonic imaging of the rotational orientation of the catheter relative to a desired location within the patient.

22 Claims, 5 Drawing Sheets

U.S. PATENT DOCUMENTS

| | | | |
|---|---|---|---|
| 5,491,198 A | 2/1996 | Shalaby et al. | |
| 5,531,713 A | 7/1996 | Mastronardi et al. | |
| 5,558,517 A | 9/1996 | Shalaby et al. | |
| 5,591,142 A * | 1/1997 | Van Erp | 604/526 |
| 5,603,327 A | 2/1997 | Eberle et al. | |
| 5,772,590 A | 6/1998 | Webster, Jr. | |
| 5,782,239 A | 7/1998 | Webster, Jr. | |
| 5,843,076 A | 12/1998 | Webster, Jr. et al. | |
| 5,928,155 A | 7/1999 | Eggers et al. | |
| 6,004,269 A | 12/1999 | Crowley et al. | |
| 6,007,488 A | 12/1999 | Jaker et al. | |
| 6,099,745 A | 8/2000 | McKenney et al. | |
| 6,123,718 A * | 9/2000 | Tu et al. | 607/113 |
| 6,246,898 B1 | 6/2001 | Vesely | |
| 6,283,947 B1 | 9/2001 | Mirzaee | |
| 6,371,915 B1 * | 4/2002 | Koger et al. | 600/445 |
| 6,375,615 B1 | 4/2002 | Flaherty et al. | |
| 6,414,086 B1 | 7/2002 | Wang et al. | |
| 6,457,350 B1 | 10/2002 | Mitchell | |
| 6,490,483 B2 | 12/2002 | Willis | |
| 6,528,199 B1 * | 3/2003 | Mercuri et al. | 429/40 |
| 6,554,801 B1 | 4/2003 | Steward et al. | |
| 6,592,580 B1 * | 7/2003 | Stockert | 606/41 |
| 6,610,005 B1 * | 8/2003 | Tao | 600/34 |
| 6,622,731 B2 | 9/2003 | Daniel et al. | |
| 6,641,540 B2 | 11/2003 | Fleischman et al. | |
| 6,661,875 B2 | 12/2003 | Greenwald et al. | |
| 6,685,657 B2 | 2/2004 | Jones | |
| 6,692,466 B1 | 2/2004 | Chow et al. | |
| 6,706,053 B1 | 3/2004 | Boylan et al. | |
| 6,716,166 B2 * | 4/2004 | Govari | 600/437 |
| 6,718,628 B2 | 4/2004 | Munshi | |
| 6,752,767 B2 | 6/2004 | Turovskiy et al. | |
| 6,765,144 B1 | 7/2004 | Wang et al. | |
| 6,841,213 B2 | 1/2005 | Parsonage et al. | |
| 6,855,124 B1 | 2/2005 | Gonzalez et al. | |
| 6,999,821 B2 | 2/2006 | Jenney et al. | |
| 7,037,271 B2 | 5/2006 | Crowley | |
| 7,220,233 B2 | 5/2007 | Nita et al. | |
| 7,285,108 B2 * | 10/2007 | Koerner et al. | 604/95.04 |
| 2003/0014100 A1 * | 1/2003 | Meens et al. | 623/1.11 |
| 2003/0018293 A1 * | 1/2003 | Tanghoj et al. | 604/19 |
| 2003/0093107 A1 | 5/2003 | Parsonage et al. | |
| 2003/0109823 A1 | 6/2003 | Hobot et al. | |
| 2003/0167056 A1 | 9/2003 | Jahns et al. | |
| 2003/0181928 A1 * | 9/2003 | Vidlund et al. | 606/151 |
| 2004/0024371 A1 * | 2/2004 | Plicchi et al. | 604/264 |
| 2004/0044286 A1 | 3/2004 | Hossack et al. | |
| 2004/0059328 A1 * | 3/2004 | Daniel et al. | 606/41 |
| 2004/0068191 A1 | 4/2004 | Seward et al. | |
| 2004/0077976 A1 | 4/2004 | Wilson | |
| 2004/0111141 A1 | 6/2004 | Brabec et al. | |
| 2004/0143160 A1 | 7/2004 | Couvillon | |
| 2004/0267156 A1 | 12/2004 | Turovskiy et al. | |
| 2005/0070844 A1 | 3/2005 | Chow et al. | |
| 2005/0234289 A1 | 10/2005 | Anstadt et al. | |
| 2005/0261670 A1 | 11/2005 | Weber et al. | |

FOREIGN PATENT DOCUMENTS

| | | |
|---|---|---|
| WO | WO 99/11182 | 3/1999 |

OTHER PUBLICATIONS

Caldwell et al, In Vitro Evaluations of Phosphonylated Low-Density Polyethylene for Vascular Application, 2002, Journal of Biomedical Materials Research Part A, vol. 6 Issue 4, p. 514-424.*

PCT International Preliminary Report and Written Opinion for PCT International Appln. No. US2006/044628, mailed May 18, 2007, (17 pages).

Abbott Cardiovascular Systems, *Final Office Action* dated Apr. 30, 2009 for U.S. Appl. No. 11/435,216.

Abbott Cardiovascular Systems, *Non-final office action* dated Sep. 10, 2009 for U.S. Appl. No. 11/435,216.

Abbott Cardiovascular Systems, *Examination Report* dated Feb. 15, 2010 for EP 06837877.7.

* cited by examiner

ECHOGENIC NEEDLE CATHETER CONFIGURED TO PRODUCE AN IMPROVED ULTRASOUND IMAGE

BACKGROUND OF THE INVENTION

The invention relates to the field of medical devices, and more particularly to echogenic catheters, such as needle catheters.

An essential step in treating or diagnosing cardiac tissue or cardiovascular diseases using an interventional catheter is the proper placement of the catheter at a desired location within the patient, which consequently requires accurate imaging of the catheter location within the patient. Although various methods of imaging catheters within a patient are possible, ultrasonic imaging (also referred to as acoustic imaging) would provide several advantages. For example, ultrasonic imaging is very safe for the expected extended time periods required for therapy guidance, unlike CT/EBCT (Electron Beam Computed Tomography) or bi-planar fluoroscopy. Additionally, ultrasound is relatively inexpensive compared to other imaging modalities such as MRI or CT/EBCT, and can provide tissue diagnostics such as wall motion and thickness information.

However, one difficulty is visualization anomalies, including artifacts and overly bright images, in the ultrasonic images of catheters. Such artifacts can provide a misleading and inaccurate impression of the shape and/or location of the catheter within the patient. Additionally, catheter elements can appear so bright and large on the ultrasonic image (called "blooming") due to their highly reflective nature relative to the anatomy, especially at the gain settings typically used to image the anatomy, that the image of the adjacent anatomy is obscured by the catheter image. For example, metallic portions of catheters can produce strong/high amplitude echoes (bright images), with a pyramid artifact (i.e., a pyramid shape of reverberation ("ringing") images trailing off in the viewing direction). Similarly, most thermoplastic catheter shafts produce strong/high amplitude direct echoes (bright images). If the gain settings of the ultrasonic imaging system are reduced to improve the image of the catheter (reduce its image and artifact brightness), the image of the anatomy fades significantly to the point of being less visible or not visible at all. Therefore, it would be a significant advance to provide a catheter with improved imaging characteristics by two-dimensional and three-dimensional ultrasonic imaging systems for enhancing the diagnosis and guidance of treatments in the body.

SUMMARY OF THE INVENTION

The invention is directed to an echogenic medical device, such as a needle catheter, which produces an improved ultrasonic image of the device, and a method of performing a medical procedure using a device of the invention. One aspect is directed to a catheter which reduces artifacts in the ultrasound image of the catheter. In one embodiment, the tip of the catheter is directly imaged over a range of angles (relative to the catheter) substantially greater than 180°. Another aspect of the invention is directed to an echogenic catheter shaft construction, in which the amplitude of the direct echoes produced by the catheter shaft are reduced, and/or in which diffuse echoes are produced that facilitates the imaging of the catheter portions that do not produce a direct echo. Another aspect of the invention is directed to an echogenic catheter in which the imaging of a portion of the catheter reveals the rotational orientation of the catheter relative to the imaging direction.

In one embodiment, the echogenic needle catheter has a spherical distal tip which reflects sonic energy more diffusely than a non-spherical distal tip. Non-spherical tips on catheters are capable of directly reflecting sonic energy back to a transducer of an ultrasonic imaging device over range of angles of not greater than about 180° relative to the longitudinal axis of the catheter. For example, catheter tips having a rounded distal end allow for direct ultrasonic imaging of the catheter tip only from the distal front of the catheter tip up to about 90° or perpendicular to each side of the catheter tip. Beyond this range, the non-curved portion of the non-spherical tips are shielded from the sonic energy by the catheter body or produce sonic reflections that do not return directly to a transducer of an ultrasonic imaging device. Thus, unlike a spherical distal tip of the invention, conventional non-spherical distal tips on catheters can't be directly imaged from substantially behind the catheter tip.

The spherical distal tip of the invention includes a spherical portion or portions that produce direct sonic reflections back to a transducer of an ultrasonic imaging device from a range of angles greater than about 180° (i.e., from a range of angles which extend from in front of to behind the catheter tip). The spherical shape is preferred for the distal tip because the spherical shape will directly reflect sonic energy at substantially the same amplitude over its direct reflection range of angles and will not have the higher amplitude and larger amplitude range of reflected echoes seen from flatter tips or the cylindrical portions of rounded tips. The spherical distal tip thus allows the tip to produce a direct ultrasonic image from a greater range of angles relative to the catheter than conventional tips. Specifically, the tip directly reflects the sonic energy back in the direction of a transducer of an ultrasonic imaging device, with the catheter located at a wide range of angles relative to the viewing direction of the ultrasonic imaging device. As a result, the distal end of the catheter can be manipulated, such as by tendon deflection or insertion into a vessel, and positioned at a greater range of angles within the anatomy yet still have its distal tip reliably imaged by an ultrasonic imaging system. Additionally, the spherical shape of the distal tip is atraumatic to prevent or inhibit disadvantageously injuring the patient's anatomy.

In a presently preferred embodiment, the spherical distal tipped echogenic needle catheter is configured for percutaneous transluminal advancement into a chamber of the patient's heart, although a variety of alternative catheter configurations may be used. The echogenic needle catheter generally comprises an elongated shaft having a proximal end, a distal end, and a needle lumen extending therein, with the spherical distal tip at the distal end of the elongated shaft, and a needle slidably disposed within the needle lumen of the catheter. In a presently preferred embodiment, the spherical distal tip has a lumen in communication with the needle lumen of the shaft and with a port in the in the spherical distal tip which is configured for having the needle slidably extend therethrough. The needle disposed within the catheter shaft has a distal end which extends distally from the spherical distal tip port in an extended configuration.

In a presently preferred embodiment, the spherical distal tip is formed at least in part of a conductive material to function as an electrode. The spherical distal tip electrode is formed at least in part of a metallic material. The metal in the spherical distal tip allows the tip to function as an electrode, primarily for diagnostic purposes, but, alternatively, for therapeutic purposes (e.g., defibrillation), if desired. Additionally, in one embodiment, the tip formed in part of a metallic material is configured to produce a tip pyramid artifact of a desired brightness and duration, as discussed in more detail below. In some embodiments, the presence of the pyramid artifact at a reduced level relative to conventional fully metallic distal tip electrodes is desirable to more reliably differentiate the image of the catheter tip from the image of the catheter body and thus indicate that the tip of the catheter is being imaged, but in a manner that doesn't substantially obscure the image of the adjacent anatomy.

Prior non-spherical distal tip electrodes reflect a large amplitude direct echo and often a large range of echo amplitudes over the range of direct reflecting angles, such that at angles behind the tip a direct echo does not return in the direction of the ultrasonic imaging device probe and, therefore, does not produce a direct image. In contrast, the spherical distal tip electrode of the invention more diffusely and evenly reflects ultrasonic energy. As a result, the spherical distal tip electrode can be imaged from a greater range of angles relative to the viewing direction of the ultrasonic imaging device (e.g., a range of angles greater than 180°; compared to a range of angles of not greater than about 180° for a conventional rounded end distal tip). Also, the echo amplitude of the tip is smaller and less variable over its range of imaging angles than a non-spherical metallic tip.

A catheter distal tip formed at least in part of a metallic material absorbs, stores and then reemits the sonic energy of the ultrasonic imaging device, causing the metal in the tip to ring like a bell, sending out ultrasonic energy until the sonic energy that it has stored is depleted. This absorbed, stored and then reemitted sonic energy is received by the ultrasonic imaging device and creates images behind the catheter tip that decrease in brightness and size as the stored sonic energy is depleted, forming the tip pyramid artifact. On the other hand, polymeric materials produce echoes from their surfaces in the body that are usually of less amplitude than the thick metallic surfaces of conventional electrode tips. Additionally, polymeric materials are generally more dissipative of sonic energy than metallic materials and thus, if any pyramid artifact is produced, it is of smaller amplitude than those produced by completely metallic tips. In one embodiment, the presence of the artifact is desirable to indicate that the tip of the catheter is being imaged. However, a disadvantageously bright/long duration/large tip pyramid artifact obscures the actual image of the catheter tip and surrounding anatomy. A distal tip of the invention, configured to minimize the amount of metallic material at the distal tip, reduces the amount of sonic energy that the tip stores and then reemits to thereby reduce the brightness and duration of the tip pyramid artifact. Additionally, in one embodiment, the spherical distal tip is in contact with a damping (sonic energy dissipating) material, such as many plastic/epoxy/elastomeric compounds and mixtures, which may contain air bubbles, tungsten filings and the like, to reduce the brightness and duration of the tip pyramid artifact. For example, in one embodiment, the spherical distal tip is filled with the damping material, and/or is connected to a proximally adjacent section of the shaft formed, at least in part, of the damping material.

In the absence of a direct echo from the tip, the only ultrasonic image of the tip may be that due to the absorbed, stored and then reemitted sonic energy and that image is located behind the actual location of the catheter tip (due to the delay in reemitting the sonic energy in the direction of the imaging device). As a result, the direct echoes produced by the spherical distal tip of the invention, from a large angular range, prevent or minimize the potential for misreading the position of the distal tip from the ultrasonic image, by avoiding the absence of an imaged direct echo from the distal tip.

In a presently preferred embodiment, the spherical distal tip is formed in part of a plastic/polymer material or materials, to minimize the amount of metal in the tip and thus reduce its echo amplitudes and reduce or eliminate its pyramid artifact. In one embodiment the distal tip has a plastic/polymer wall formed of a material selected from the group consisting of an epoxy, a polyurethane, a silicone, a polyethylene, and an ethylene acrylic acid functionalized polyolefin such as PRIMACOR. In a presently preferred embodiment, the tip is formed at least in part of an adhesive polymer such as PRIMACOR to assure the secure bonding together of metals to polymers or polymers to polymers in many configurations of the spherical tip, especially bonding plastics/polymers to metallic components such as hypotubes, metal shells or to thin coatings/platings of metallic conductors. Adhesive polymers may be incorporated into a spherical tip assembly in a number of ways. For instance, adhesive polymers may be mixed with another polymer to provide that polymer with adhesive characteristics or the adhesive polymer may be put into solution and applied to a surface (i.e. by dipping, spraying, brushing), such that when the solvent evaporates, a thin coating of the adhesive polymer is deposited on the surface to provide an adhesive surface for further processing. The adhesive function of the adhesive polymers is often enhanced by raising the temperature of the adhesive polymer for a short time (i.e. during a molding or forming process, as part of a conditioning cycle) and, thus are often referred to as "hot melt adhesives".

For example, in one embodiment, the spherical distal tip includes a metallic member therein with an exposed surface to function as an electrode. In another embodiment, the spherical outer surface of the tip is defined by a wall formed of a mixture of blended or otherwise combined polymeric and metallic materials. In another embodiment the spherical tip is formed of a polymeric material or materials and/or a mixture of polymeric and metallic materials and at least a portion of its outer surface is a thin metallic layer or layers, which may be deposited or attached by various conventional methods (i.e. sputtering, deposition processes in chemical solutions, pressure bonding). However, a variety of suitable configurations can be used, including a spherical tip formed of a wall of metallic material (although a metallic wall preferably defines a spherical interior chamber to minimize the amount of metal in the tip and thereby reduce the brightness and duration of the tip pyramid artifact). In embodiments in which the wall of the spherical distal tip defines a spherical interior chamber, the chamber is preferably filled with a polymeric material.

In a presently preferred embodiment, the spherical distal tip comprises a wall with a curved outer surface formed at least in part of a polymeric material and having a metallic pin member therein, or having a metallic outer layer thereon.

In one embodiment, an element(s) formed at least in part of a metallic material such as an additional conductive electrode(s) or marker(s) provided on the shaft is proximally spaced a sufficient distance from the spherical distal tip that the ultrasonic images produced by these additional metallic elements do not overlap with those of the spherical distal tip. As a result, the catheter of the invention facilitates accurately interpreting the spherical distal tip's position in the ultrasonic images. Such additional electrodes or markers may also be constructed of a limited amount of metal and/or in contact with sonic energy damping materials to provide the same brightness and artifact reduction benefits as previously described in relation to the spherical tip.

In one embodiment, a catheter of the invention has an outer jacket layer along at least a portion of the catheter shaft, formed of an impedance matching material of approximately a quarter or three quarter wavelength thickness. In one presently preferred embodiment, the layer has a quarter wavelength thickness in order to maximize the destructive interference. However, because the ultrasonic pulse waveform sent out by many echo probes is often many wavelengths long, a three quarter wavelength thickness will also produce destructive interference and can be reasonably effective in reducing the amplitude of reflected sonic energy. For example, in an embodiment in which the center frequency (imaging ultrasonic transducers typically send out sonic pulses that contain a spectrum of sonic frequencies) of the displayed echoes is high and/or the speed of sound in the material is too low, then the material thickness of the jacket might be too small to be efficiently produced/installed at a quarter wavelength thickness. For example, at 6 MHz, silicone has a quarter wavelength thickness of about 0.0015", which may be difficult to process/control, but has a three quarter wavelength thickness of about 0.0045", which facilitates accurately producing the outer jacket layer. Echo TTE and TEE systems, applicable to this technology, are advertised to operate in frequency ranges that go from about 1 MHz to 12 MHz, and a typical cardiac transducer (probe) is advertised to operate in a 2-4 MHz range or in a 3-8 MHz range.

The outer jacket layer is formed of a material with an acoustic impedance which more closely matches that of blood than does the material(s) forming the portions of the catheter shaft underneath the outer jacket layer. "Acoustic impedance" is a material property which may be defined as the velocity of sound in that material multiplied by the density of the material. For example, in one embodiment, the outer jacket layer is formed of a polymer selected from the group consisting of elastomeric polymers, low density polyethylene (LDPE), and ethylene vinyl acetate (EVA), and the underlying catheter shaft comprises a metallic braid or other metallic configuration, and/or a high acoustic impedance polymer or thermoplastic polymer more commonly used to form catheter shaft outer surfaces, e.g., nylons, Pebax, polyethylenes, polyesters, etc. In some embodiments, the outer jacket is coated with a lubricant (i.e. silicone oil based coatings like MDX) or a hydrophilic or a hydrogel coating to substantially reduce the friction and abrasive properties of the outer jacket (hydrophilic or hydrogel coatings must be wetted to reduce the friction and abrasive properties). Preferred practical outer jacket materials are most often soft/elastomeric/low modulus in nature and have rather high coefficients of friction, which may make them difficult to insert into the vasculature and more abrasive to the vasculature than desired, thus, requiring such coatings. Additionally, an irregular/bumpy/dimpled outer jacket OD and/or ID surface is preferred to provide a more scattered echo reflection and thus facilitate imaging of the cylindrical shaft at angles that would not produce a direct echo if the shaft were smooth. As a result of the outer jacket material choice, the reflection of sonic energy off the outer surface of the catheter shaft is reduced from that which otherwise results from a larger acoustic impedance mismatch between blood and the catheter shaft outer jacket. Thus, the outer jacket layer couples more of the ultrasonic energy into the catheter, so that a larger portion of the sonic energy penetrates the outer jacket layer and is transmitted through the catheter or into the shaft of the catheter and less sonic energy is reflected from the surface of the outer jacket. In another embodiment, the outer jacket includes a material/filler (i.e. tungsten fillings) that improves the sonic energy dissipation properties of the outer jacket material to reduce the amplitudes of echoes reflected by the internal portions of the catheter shaft. Sonic energy will pass through the outer jacket to be reflected by the internal portions of the catheter shaft and then back through the outer jacket again to be received by the imaging device and thus imaged. The more dissipative the outer jacket, the less of this sonic energy will be returned to the imaging device. In many embodiments, the material or filler included in the outer jacket also causes the catheter shaft to more diffusely reflect a portion of the sonic energy that penetrates the jacket back to the imaging device, such that portions of the cylindrical catheter shaft that do not produce a direct echo may be more easily imaged. Such materials/fillers may also improve the imaging of the shaft by other imaging modalities, such as fluoroscopy.

In outer jackets with irregular/bumpy/dimpled surfaces, it is preferred that the thickness of the flatter surfaces of the jacket be kept near the ¼ wavelength thickness to reduce the amplitude of the direct reflection. It should be noted that current ultrasonic imaging systems/devices may filter out the lower frequencies to improve the resolution of the displayed image, called harmonic imaging, and which therefore affects the thickness of the quarter or three quarter wavelength outer jacket (a quarter or three quarter wavelength outer jacket thickness is twice as thick at 3 MHz than it is at 6 MHz). In general, an outer jacket thickness in the 0.001" to 0.008" range is preferred. Below/near 0.001" and coverage of metallic braids or other internal shaft components is uncertain and processing of the jacket tubing becomes a challenge. Above/near 0.008" and the jacket tends to disadvantageously increase the overall profile of the catheter. An elastomeric jacket used to form the outer jacket layer has the property of being expandable (i.e. by air pressure), such that it may be easily extruded as a tube with a wall thickness that is too thick, but then expanded and installed on a shaft in the expanded condition, which reduces the wall thickness to a desired thickness.

By producing destructive interference between the reflected waves from the OD and ID surfaces of the outer jacket, the quarter or three quarter wavelength layer reduces the amount of directly reflected sonic energy from the catheter shaft surface that may be received by the ultrasonic imaging device. Thus, the quarter or three quarter wavelength matching layer reduces the displayed brightness of the catheter body image, to thereby avoid obscuring the image of the adjacent anatomy (e.g., cardiac tissue) and avoid producing a pronounced curved body artifact as discussed in more detail below.

Unlike prior quarter wavelength matching layers provided on transducers to improve the transmission of sonic energy from the transducer into the blood and tissue of the patient's body (and also in the opposite direction), a catheter embodying features of the invention has a quarter or three quarter wavelength matching layer extending along a section of the catheter shaft which is not an electrical to sonic energy and/or a sonic to electrical energy transducer. Thus, catheter has a quarter or three quarter wavelength matching layer which is specifically configured to reduce the direct sonic reflections from a catheter shaft (and which is not configured to more efficiently couple sonic energy into and out of a transducer).

In a presently preferred embodiment, the outer jacket is formed of a mixture of two elastomeric compounds, styrene butadiene styrene and polyurethane, which is extruded into a tube under conditions that produce an irregular and bumpy OD and a smooth ID. The jacket, when installed on a catheter shaft, diffusely reflects sonic energy (low amplitude), allowing the entire shaft covered by the jacket to be imaged and not just the shaft portions that produce a direct echo. Additionally, the direct echo portions of the shaft produce a much reduced image brightness compared to conventional catheter shafts. Also, the jacket eliminates the ringing artifact from a metallic (e.g., NiTi) cage portion of the shaft located at the distal end of the shaft.

By reducing the amplitude of the direct echoes reflected by the catheter shaft and received by the imaging device, the curved body artifact of the catheter shaft is also reduced. Most ultrasonic imaging devices contain an array of small ultrasonic transducers to send and receive ultrasonic energy to form images. These small ultrasonic transducers send most of their sonic energy out in a direction that is generally perpendicular to the surface of the transducer, but, especially in small transducers, a considerable amount of sonic energy also goes out in other directions in a manner commonly referred to as "side lobes". With a conventional highly reflective (high amplitude echo producing) cylindrical catheter shaft, the reflections of these side lobes that return to the imaging device of a 3D echo system from the direct reflecting surface portion of the catheter shaft produces a bright curved image that may be mistaken for an image of the catheter shaft. Additionally, the bright curved image may obscure the images produced by the relatively low amplitude diffuse echoes that may be received by the imaging device from other portions of the catheter shaft, and may also obscure the images of adjacent tissues. By reducing the amplitude of the echoes directly reflected by the catheter shaft, this bright curved image artifact is reduced in size and brightness, while the image brightness of the diffuse echoes from other portions of the shaft and from the tissues are less impacted (ultrasonic imaging systems are designed to amplify low amplitude echo signals more than higher amplitude echo signals).

One aspect of the invention is directed to a method of performing a medical procedure using a spherical distal tipped echogenic needle catheter of the invention. The method generally comprises advancing within a patient's anatomy an echogenic needle catheter comprising an elongated shaft, a spherical distal tip which is preferably formed at least in part of a conductive or metallic material and which has a port at a distal end of the spherical distal tip, and a needle which extends distally from the spherical distal tip port in an extended configuration. The method includes directing sonic energy at the spherical distal tip from an ultrasonic imaging device, such that the spherical distal tip more diffusely reflects the sonic energy than at least a portion of a non-spherical distal tip, to produce an ultrasonic image of the distal tip within the patient.

It is preferred that the catheter be constructed in a manner that allows the catheter lumens to be flushed with water based solutions and avoids air filled voids in the catheter shaft. In one embodiment, the method includes filling the catheter lumens with an aqueous fluid, so that the catheter has a plastic-aqueous fluid interface which reflects less of the sonic energy than the plastic-air interface present in the absence of the aqueous fluid. The plastic-air interface is a stronger reflector of sonic energy than the plastic-blood or plastic-water interface. As a result, the fluid-filled catheter of the invention reduces the amount of sonic energy which is reflected back in the direction of the ultrasonic imaging device probe by enhancing the amount of sonic energy which instead penetrates the catheter and travels through the catheter to exit the catheter on the other side of the catheter directed away from the ultrasonic imaging device probe, and/or by enhancing the amount which is absorbed by the catheter material and diffusely reemitted or dissipated. As a result, the catheter curved body artifact, which can be mistakenly interpreted as illustrating an arching or bending length of the catheter body, is reduced. Thus, the standard Cath Lab practice of filling the catheter lumen(s) with water-based solutions (usually heparinized saline or fluoroscopic contrast) prior to insertion into the body, although usually not sufficient to make a catheter's shaft reflect a sufficiently low amplitude echo to eliminate or adequately reduce the curved body artifact, is nonetheless desirable for ultrasonic imaging.

An alternative embodiment is directed to an echogenic catheter, such as a needle catheter, with echogenic portions arranged in an array to facilitate determination by ultrasonic imaging of the rotational orientation of the catheter relative to a desired location within the patient. In one preferred embodiment, the rotational orientation echogenic portions are on a transvascular needle catheter generally comprising an elongated shaft having a needle lumen in communication with a needle distal port located proximal to the catheter shaft distal end, and a needle in the needle lumen configured for slidably extending through the needle distal port in the catheter shaft. The rotational orientation echogenic portions are more highly reflective than the shaft material adjacent to the portions, and are arranged in an array in which each adjacent pair of portions are circumferentially and longitudinally spaced apart from one another. The rotational orientation echogenic portion(s) oriented toward the ultrasonic imaging device probe will produce the brightest image. The position of the ultrasonic imaging device probe relative to the ultrasonic image of the catheter is shown on the display along with the anatomy. As a result, the rotational orientation of the catheter relative to the anatomy can be determined by the ultrasonic image.

One aspect of the invention is directed to a method of performing a medical procedure generally comprising advancing within a patient's body lumen an echogenic needle catheter having rotational orientation echogenic portions on an outer surface of a section of the catheter shaft, and determining the rotational orientation of the catheter relative to a desired location in the body lumen by directing ultrasonic energy at the shaft section from an ultrasonic imaging device. The sonic energy produces an ultrasonic image of the shaft section in which the rotational orientation echogenic portions do not all appear with an equal brightness for a given orientation. In a presently preferred embodiment, this is used to adjust the rotational orientation of a transvascular catheter's needle distal port within a patient's coronary blood vessel, such as a coronary sinus, vein or artery, to direct the needle into the desired heart tissue and avoid puncturing the free wall of the vessel or puncturing adjacent vessels. The array of rotational orientation echogenic portions typically is formed by two or more, and more preferably three or more echogenic portions. As a result, depending on the circumferential spacing of the rotational orientation echogenic portions, multiple rotational orientation echogenic portions are typically visible in any given ultrasonic image of the catheter but with a different brightness depending on the rotational orientation of the portions relative to the viewing direction of the ultrasonic imaging device. Thus, detailed rotational orientation information is obtained from the ultrasonic image by comparing it to the known layout of the array of rotational orientation echogenic portions. The catheter thus facilitates adjusting the rotational orientation of the catheter within the patient, to accurately position the needle at the desired heart tissue, and avoid adjacent vessels or puncturing the free wall of the vessel.

Thus, one embodiment of the invention is directed to an echogenic catheter configured to reduce or even out artifacts in the ultrasonic image of the catheter (e.g., by correcting inaccuracies in the image shape and/or location of the catheter or components of the catheter, in addition to making the images less bright). In one embodiment, a catheter of the invention has a spherical distal tip which is directly imaged over a range of angles (relative to the catheter) substantially greater than 180°. In another embodiment, an echogenic catheter of the invention allows for the determination by ultrasonic imaging of the rotational orientation of the catheter relative to the patient's anatomy by providing an array of portions of the catheter that have different echogenic properties/image viewing properties. These and other advantages of the invention will become more apparent from the following detailed description and exemplary drawings.

DETAILED DESCRIPTION OF THE INVENTION

Figure 1:
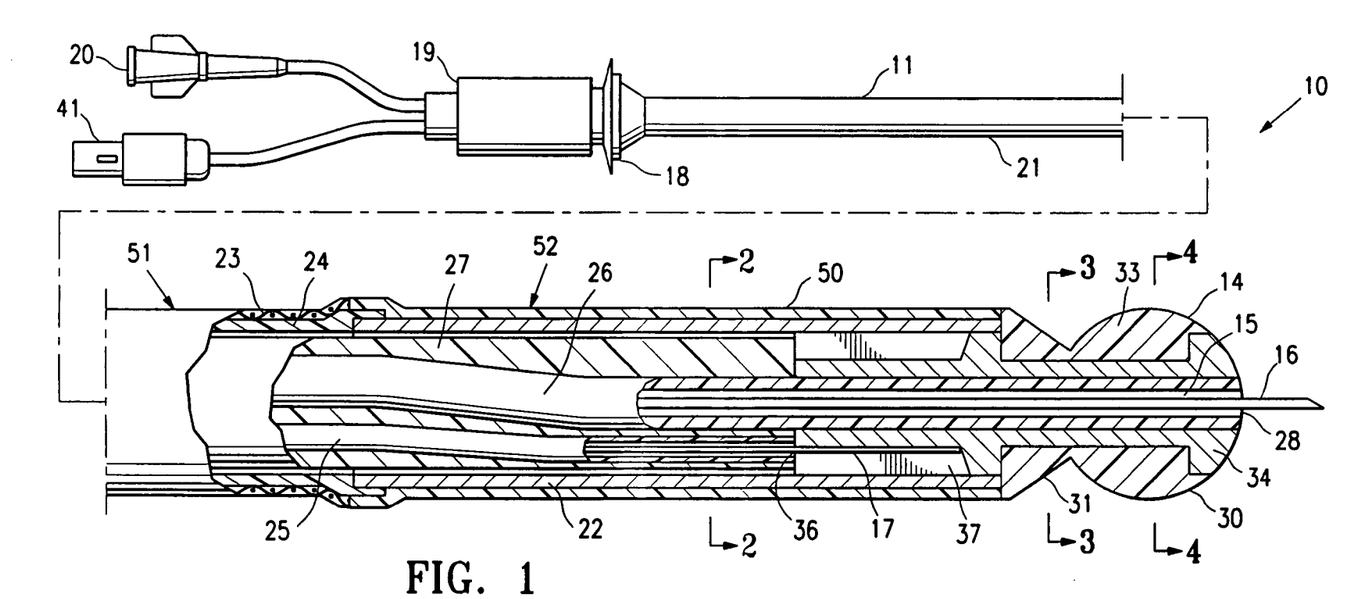
FIG. 1 is an elevational view, partially in section, of an echogenic needle catheter embodying features of the invention, having a spherical distal tip.
Figure 2:
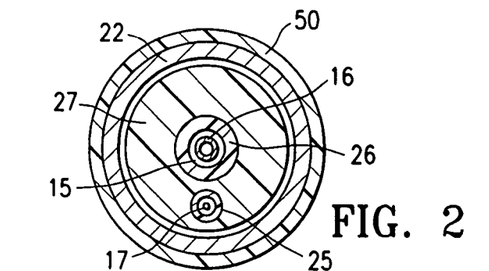
FIGS. 2-4 are transverse cross sectional views of the catheter of FIG. 1, taken along lines 2-2, 3-3, and 4-4, respectively.
Figure 3:
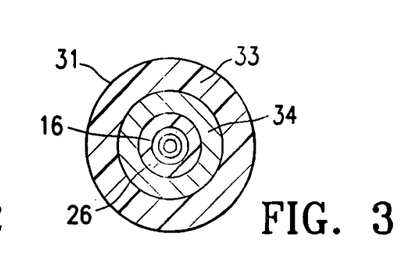
Figure 4:
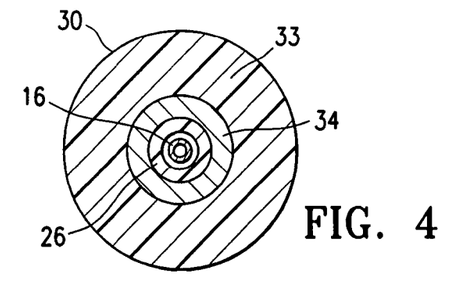

FIG. 1 illustrates a needle catheter which embodies features of the invention. In the embodiment illustrated in FIG. 1, the needle catheter 10 comprises an elongated shaft 11 having a proximal shaft section and a distal shaft section and a needle lumen 15, and a spherical distal tip 14 at the distal end of the shaft 11. A needle 16 is slidably disposed within the needle lumen 15 of the shaft, with an extended configuration in which the needle distal end extends distally from the distal end of the shaft (see FIG. 1), and with a retracted configuration (not shown) in which the needle distal end is proximally retracted into the catheter lumen. In the illustrated embodiment, the catheter 10 has a deflection member 17 (e.g., a tendon wire) connected to a deflection control mechanism 18 at a proximal adapter 19, for deflecting the distal end of the catheter 10. To effectively deflect the distal end of the catheter the deflection member 17 is preferably near the surface of the shaft in the deflecting (curving) portion. However, a catheter having a spherical distal tip in accordance with the invention can have a variety of suitable catheter configurations including a non-deflecting configuration. The proximal adapter 19 on the proximal end of the shaft has a port 20 configured for providing access to the needle 16 for delivery of an agent, or for aspiration, through the lumen of the needle 16. A variety of operative connectors may be provided at the proximal adapter depending on the desired use of the catheter 10. FIGS. 2-4 illustrate transverse cross sectional views of the catheter 10 of FIG. 1, taken along lines 2-2, 3-3, and 4-4, respectively.

In the embodiment of FIG. 1, the shaft comprises a tubular body member 21, which in one embodiment has a relatively flexible distal portion 52 and a relatively less flexible proximal portion 51. A variety of suitable catheter shaft designs can be used with the spherical distal tip of the invention, including deflectable needle catheter shafts described in U.S. Ser. No. 10/676,616, incorporated by reference herein in its entirety. The proximal portion 51 is typically formed at least in part of metal, such as a polymer reinforced with a braided or coiled metallic filaments or a hypotube or slotted metallic tube, although it may alternatively or in addition consist of a high modulus polymer. In the illustrated embodiment, the shaft 11 has a braided body layer 23 extending distally from a proximal end section of the catheter, and comprising a polymeric material encapsulating a wound tubular support layer typically formed of braided filaments of a metal such as stainless steel. The braid is encapsulated by an outer layer which is typically formed of multiple sections of differing durometers/polymers joined end to end to provide a stiffness transitions along the length of the catheter. The braid is formed over a polymeric core layer 24.

In the illustrated embodiment, the distal portion 52 of the tubular body member 21 of the shaft 11 comprises a cage typically formed of a slotted metallic tube. The compression cage 22 is configured to deflect laterally as discussed in the '616 application, incorporated by reference above. The cage 22 is typically covered with an outer jacket layer 50, which in one embodiment is an impedance matching quarter wavelength layer as discussed in more detail below. In other embodiments, the cage 22 may be a wire, wires, a construction of wires, a thin metallic strip(s) or a combined construction that provides a restoring force to the deflection distal section of the shaft 11.

An inner tubular member 26 extending within the tubular body member 21 defines the needle lumen 15 of the shaft. The inner tubular member 26 is formed of a single layered, integral one-piece tube extending from the proximal to the distal end of the catheter, or alternatively of multiple sections of tubing with communicating lumens, and/or a multilayered tube(s). The deflection member 17 extends within a lumen of a second inner tubular member 25, and is secured to the shaft adjacent to the distal end of the distal portion 52 of tubular body member 21. In the illustrated embodiment, a stabilizing tubular member 27, typically comprising a dual lumen extrusion, is positioned within at least a section of the cage 22 to stabilize the position of the inner tubular members 25, 26 therein. The stabilizing member 27 is formed of a single section or multiple longitudinally adjacent sections of the tubing, and has a proximal end typically located within the cage 22 or a short distance proximal thereto. In one embodiment, the acoustic impedance of both the outer jacket and distal catheter shaft polymers (polymer mixtures) is adjusted using tungsten filings to attain both a low direct resultant reflected echo amplitude, but also the desired visibility under fluoroscopy. The stabilizing tubular member 27 may be processed in conjunction with the cage 22 such that the cage 22 is coated or covered by the material of the stabilizing tubular member 27. This coating or covering of the metallic cage 22 (or wire(s) or strip(s)) provides a more even acoustic impedance (places where metal is versus places where metal isn't) to the inside of the shaft for the outer jacket 50 to be matched to, as will be discussed in more detail below. In alternative embodiments, the stabilizing tubular member 27 is omitted.

The catheter spherical distal tip 14 extends distally of the distal outer surface of the shaft, and has a spherical portion 30 and a proximal support portion 31 which has a proximal end connected to the distal end of the distal portion 52 of tubular body member 21. In a presently preferred embodiment, a proximal end section of the distal tip 14 is bonded, for example using an adhesive, to the inner surface of the cage 22, although a variety of suitable configurations can be used to attach the spherical distal tip including a spherical distal tip formed integrally with the shaft 11.

The spherical portion 30 has a curving outer surface extending around the circumference of the distal tip to an included angle substantially greater than 180°. The outer diameter of the spherical distal tip 14 is a rigid (i.e., non-collapsing/expanding) outer diameter, which is typically approximately equal to the outer diameter of the distal portion 52 of the tubular body member 21 to provide the greatest range of imaging angles. The spherical distal tip 14 has a lumen extending therethrough which forms a distal section of the needle lumen 15 and which is in communication with a port 28 at a distal end of the spherical distal tip 14. In the embodiment illustrated in FIG. 1, a distal section of the inner tubular member 26 defines the lumen within the spherical distal tip 14. However, a variety of suitable configurations may be used including an embodiment in which the distal end of the inner tubular member is proximal to the distal end of the catheter.

In the illustrated embodiment, the proximal support portion 31 has a conically shaped section with an outer surface tapering distally to a smaller outer diameter. The support portion 31 is formed of a sufficiently strong material(s) to securely connect and support the spherical distal tip 14 during use of the catheter 10. The length and tapering angle of support portion 31 is preferably chosen such that it will not shield or block the spherical distal tip portion 30 from sonic energy over the designed range of distal tip imaging angles. Additionally, the spherical distal tip portion 30 and support portion 31 are configured to avoid catching on portions of the anatomy (i.e. valve to papillary muscle chordae) or on portions of the insertion devices (i.e. an introducer, a guide catheter) during positioning or withdrawal. Specifically, the tapers and curved surfaces of the spherical distal tip portion 30 and support portion 31 are designed limit the forces that may be applied to the anatomy or other devices by the spherical distal tip 14 before the catheter deflects enough to disengage from the obstruction.

Figure 5:
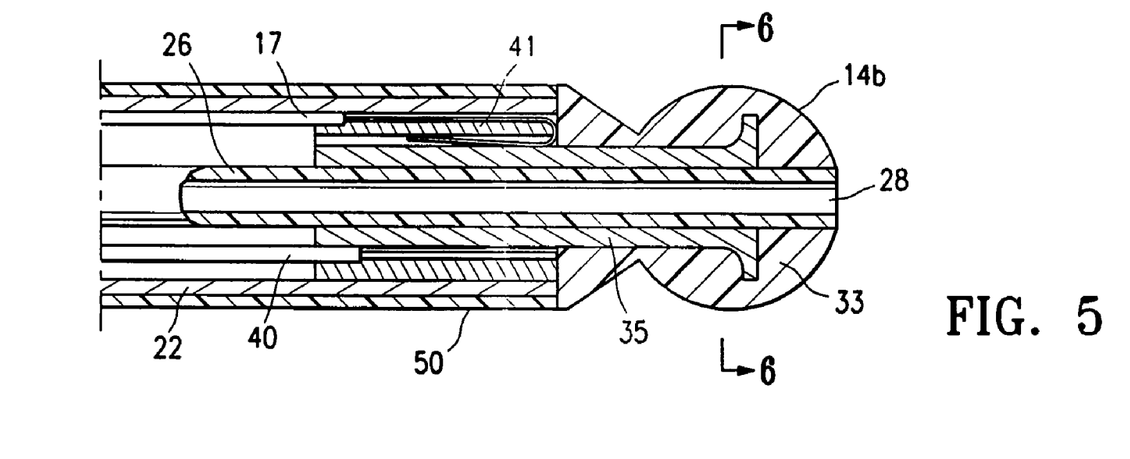
FIG. 5 is a longitudinal cross sectional view of an alternative embodiment of the spherical distal tip having a hypotube connecting member.

In a presently preferred embodiment, the tip assembly is insert molded of a polymer/plastic 33 around a high strength support member such as a machined hollow pin 34 (see e.g., FIG. 1), or short length of stainless steel hypotube 35 with a flared end at/near the center of the spherical tip (see e.g., FIG. 5). The plastic material 33 is a damping material to dissipate sonic energy at the tip 14. The conical portion 31 of the tip assembly is typically molded from the same material as the spherical portion 30, and a portion of the pin 34 or hypotube 35 extends proximally out of it.

Once mounted on the catheter, the proximal end of the pin 34 or hypotube 35 resides inside the catheter shaft 21 and attaches the tip assembly to the distal end of the catheter shaft. Thus, while the tip assembly has a substantial metallic portion (i.e., the pin 34 or hypotube 35), it is covered and in contact with a plastic that has damping qualities, and it has at least a section not exposed directly to the sonic energy, to limit its impact on the ultrasonic imaging of the tip. The catheter tip 14 is configured for mechanically strong, secure attachment and support, while nonetheless minimizing the amount of metal at the catheter distal end in order to minimize the brightness and duration of the tip pyramid artifact in the ultrasonic image of the catheter distal end.

The spherical distal tip 14 preferably functions as an electrode, and thus has a conductor (e.g., a metal wire) electrically connected thereto. In the embodiment illustrated in FIG. 1, the deflection member 17 is electrically connected to the pin 34 so that the member 17 doubles as a deflection and a conduction wire. However, a variety of suitable configurations can be used including embodiments in which a separate conduction wire is provided which extends the entire length of the catheter or which extends between the deflection member and the spherical distal tip. Therefore, it should be understood that in alternative embodiments, the shaft 11 may include a separate conductor lumen extending within the tubular body member 21. The conduction wire is soldered, welded, mechanically crimped or imbedded or otherwise electrically connected to the spherical distal tip 14.

At least a second electrode 49 (see potential locations in FIG. 8) is typically provided on the shaft 11, with a corresponding electrical conductor. The second electrode, functions, for example, as a reference electrode for the spherical distal tip electrode. The second electrode is preferably provided on the proximal portion 51 of the tubular body member 21 so that it is located out of the heart chamber, preferably superior to the heart chamber, such as in the aortic arch or a vena cava, for tip tissue contact/tissue ECG monitoring applications and/or about one centimeter behind the tip for ECG anomaly detection applications. In applications where pacing is anticipated to be required, many electrodes may be spaced along the distal portion of the catheter shaft, such that, at least, one electrode (with a surface electrode) or electrode pair will pace successfully at the current catheter position. The conductor wire(s) electrically connect to an electrical connector 41 which is provided at the proximal adapter 19 for connecting the catheter 10 to diagnostic or therapeutic equipment (not shown).

In the embodiment illustrated in FIG. 1, the metallic pin 34 has a proximal end 36 electrically connected to the deflection/conductor member 17 and has an exposed distal end at the distal end of the spherical distal tip 14 to form the distal tip electrode. The pin 34 has two grooves (illustrated with broken lines in FIG. 1) on opposite sides of the proximal section of the pin 34, and the distal end of the deflection/conductor member 17 is within one of the grooves.

Figure 6:
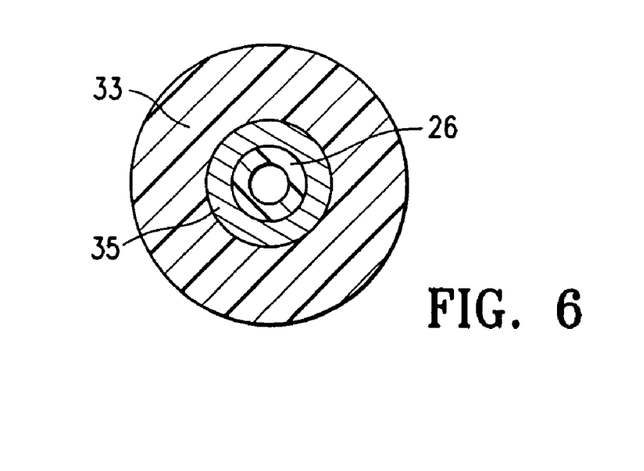
FIG. 6 is a transverse cross sectional view of the catheter of FIG. 5, taken along line 6-6.

FIG. 5 illustrates an alternative embodiment in which spherical distal tip 14*b* has a hypotube 35 which does not have an exposed distal surface. As a result, to function as an electrode, at least a portion of the outer surface of polymeric layer 33 of the tip 14*b* is coated or otherwise provided with a conductor (metallic) outer layer(s) such as, for example, a gold outer layer and a copper inner layer. The conductor (metallic) coating is very thin, and is not illustrated in FIG. 5. The thin metallic coating(s) on the tip has too little mass/size to store much sonic energy, and is also in contact with the damping plastic, and is so thin that a part of its reflective properties are determined by the properties of the plastic behind it. The thin metallic coating(s) (not shown) form a wall preferably having a spherical outer surface, and a spherical inner surface defining a spherical interior chamber, with the plastic 33 filling the spherical interior chamber around the needle lumen of the spherical distal tip. FIG. 6 illustrates a transverse cross section of the tip 14b of FIG. 5, taken along line 6-6.

In the embodiment illustrated in FIG. 5, a separate conduction wire 40 is electrically connected to the hypotube to electrically connect to the outer conductor (metallic) coating. A band 41, typically formed of metal, connects the deflection member 17 between the hypotube 35 and the cage 22, in the illustrated embodiment. Although not illustrated in FIG. 5, the shaft would typically include a needle 16 in inner tubular member 26, and one or more additional inner tubular members, which are similar to inner tubular member 25 of FIG. 1, and which contain the deflection member 17 and/or conduction wire 40 in the embodiment of FIG. 5.

Figure 7:
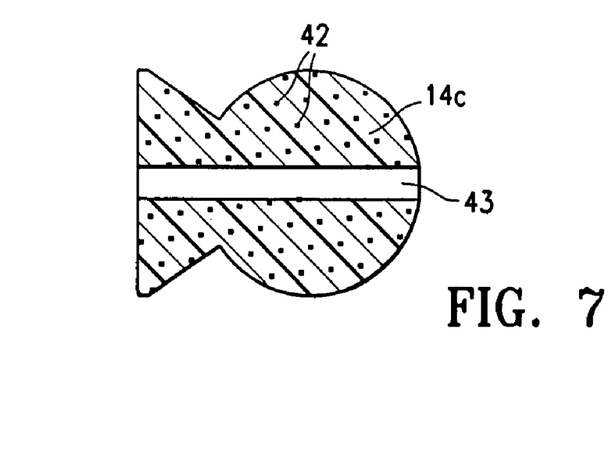
FIG. 7 is an elevational view, partially in section, of a distal end section of an alternative spherical distal tip configuration.

FIG. 7 illustrates a longitudinal cross sectional view of an alternative embodiment of a spherical distal tip 14c embodying features of the invention, having a wall formed of a mixture of a polymeric material and a metallic material 42. The mixture is blended or otherwise combined and comprises a sufficient amount of metallic material 33 so that the spherical distal tip 14 functions as an electrode when electrically connected to diagnostic or therapeutic equipment. In a presently preferred embodiment, the polymer/metallic material mixture has about 80% to about 98% metallic materials 33 by weight. A variety of suitable materials can be used including metallic materials 33 selected from the group consisting of tungsten, tungsten iridium, stainless steel, gold or platinum and a variety polymeric materials are suitable including those selected from the group consisting of epoxies, silicones and thermoplastics.

In the embodiment of FIG. 7, the wall of the distal tip 14c has a spherical outer surface and an inner surface defining a needle lumen 43 within the spherical distal tip, so that the tip 14c has a thickened wall portion which fills the space between the needle lumen 43 therein and the spherical outer surface of the distal tip 14c. The lumen 43 defined by the wall is configured for being in communication with a proximal section of the needle lumen 15 of the inner tubular member 26, or, alternatively, for receiving a tubular member such as a distal section of the inner tubular member 26 or a separate tubular member.

Thus, in the embodiment illustrated in FIG. 7, the polymer/metallic mixture is molded or otherwise shaped to form the spherical distal tip wall extending from the outer to the inner surface of the tip 14. Alternatively, the metal/polymer mixture can be used to form an outer layer on a spherical distal tip similar to the embodiment discussed in relation to FIG. 5. Polymer/metal mixtures which contain a sufficient amount of polymer to facilitate working with the mixture typically do not contain a sufficient amount of metal to be conductive. Therefore, In a presently preferred embodiment, such polymer/metallic material mixtures are made conductive by first mixing the metallic material with the polymer or the polymer parts while the polymer or the polymer parts are in a liquid state, and the non-conductive mixture is then applied to the spherical tip, and the tip is subjected to heat and pressure in a mold constructed to allow the polymer to flow out of the mold while most of the metallic material is retained within the mold. In this way the concentration of the metallic material is raised to the point that many of the metallic material particles contact each other and thus, a conductive layer is former on the spherical tip (or also on other portions of the tip). Several cycles of the addition of the non-conductive mixture and the re-application of heat and pressure may be required in some processes to create a conductive tip of the desired shape and dimensions.

The spherical distal tip 14 has a uniformly curving outer surface extending around the circumference of the tip 14. The outer diameter of the spherical distal tip 14 is preferably equal to or less than the outer diameter of a portion of the shaft 111 which defines the distal outer surface of the shaft proximally adjacent to the spherical distal tip 14 (although the outer diameter of the spherical portion 30 of the distal tip 14 is greater than a distal section of the conically shaped portion 31). Minimizing the outer diameter (OD) of the distal tip 14 so that it is not greater than the OD of the catheter shaft is preferable in order to minimize the size of the introducer (OD/ID) required at the catheter insertion site which has to accommodate the catheter therein. A larger introducer OD causes a larger puncture wound, which studies have shown have a greater incidence of complications such as pain, bleeding, infection and extended healing times. Typical catheters used to inject substances may range in size from about 4 F (about 1.3 mm OD) for vessel needle or other injections to about 9 F (about 3 mm OD) for ventricular needle or other injections. The spherical portion 30 of the distal tip may have a smaller radius than catheter body radius to help minimize the brightness and duration of the echo and tip pyramid artifact of the ultrasonic image, however; all other things being equal, the smaller the radius of the spherical distal tip, the smaller the range of angles from which that tip may be imaged.

Although generally not preferred due to concerns regarding effective sterilization, an alternative spherical distal tip (not shown) can have a hollow structure with a spherical wall defining a hollow interior chamber (i.e., not filled with plastic 33) and optionally formed of metal or a polymer-metal blend to function as a distal tip electrode.

Figure 8:
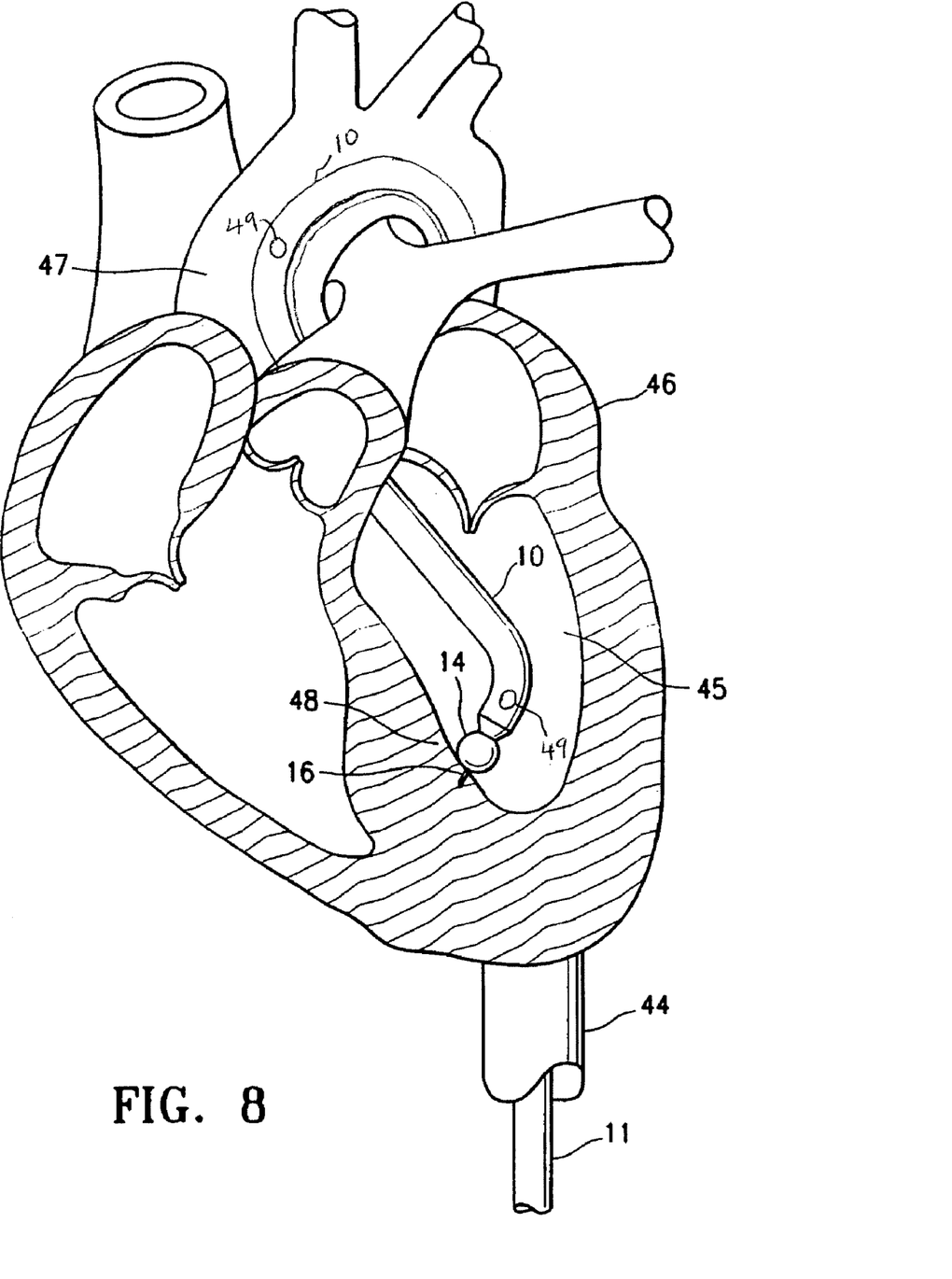
FIG. 8 illustrates the catheter of FIG. 1 within a left ventricle of a patient's heart.

FIG. 8 illustrates the needle catheter 10 with the distal end of the catheter 10 within the left ventricle 45 of the patient's heart 46. The catheter 10 is typically advanced in a retrograde fashion within the aorta 47, via the lumen of an introducer sheath which is inserted into the femoral artery. The catheter 10 illustrated in the embodiment of FIG. 1 is not configured for advancement over a guidewire, although in alternative embodiments and delivery sites, such as into veins or arteries, a guidewire lumen is provided in the shaft 11 for slidably receiving a guidewire therein. Additionally, in such vessel applications, the guidewire and catheter may be inserted into position using a guiding catheter that is first inserted into the introducer. In this intracardiac application, a deflecting mechanism is desired. By activating the deflection member 17 using the deflection control mechanism 18 the distal end of the catheter is caused to deflect away from the longitudinal axis of the shaft 11. With the distal end of the spherical distal tip 14 thus positioned in contact with a desired site of the ventricle wall, electrical data can be collected from the spherical distal tip electrode 14. The electrical data (e.g., tissue contact ECG) facilitates tissue diagnostics (in combination with echo image ventricle wall motion measures) to determine if the site should be treated or not. The site can be treated by direct injection of a therapeutic agent, such as a biological or chemical agent, from the needle 16. FIG. 8 illustrates the distal end of the spherical distal tip 14 and the port 28 against the ventricle wall, with the needle 16 in the extended configuration advanced out the port 28 and into the cardiac tissue 48 of the ventricle wall. Multiple sites within the left ventricle can be thus accessed and treated using the catheter of the invention.

Although illustrated in the ventricle, a catheter of the invention can be used to inject into the vessel wall or through the vessel into the myocardium or other adjacent tissues. Thus, although the distal needle port 28 is in the distal-most end of the spherical distal tip 14 coaxial with the longitudinal axis of the catheter in the embodiment of FIG. 1 (with the needle extending aligned with the longitudinal axis of the catheter), in alternative embodiments (not shown; e.g., those for injecting into or through a vessel) the catheter 10 has a needle port configured to direct the needle at an angle away from the longitudinal axis of the catheter. For example, the port through which the needle extends can be located eccentric to the longitudinal axis of the catheter or in a side wall of the catheter proximal to the distal end of the spherical distal tip.

Ultrasound can be used in conjunction with the catheter supplied ECG to provide tissue diagnostics by visualization of the wall motion and thickness. Additionally, the catheter 10 facilitates using ultrasonic imaging for visualization and positioning of the catheter 10. Specifically, with the catheter 10 distal end in the left ventricle (or other desired location within the cardiac anatomy), sonic energy is directed at the spherical distal tip 14 from an ultrasonic imaging device (not shown). The ultrasonic imaging device is typically an external device, a TTE probe (Transthoracic Echo, probe on the chest), although a TEE probe (Transesophageal Echo, probe in the throat), an ICE probe (Intracardiac Echo, probe in a cardiac chamber) or an IVUS (Intravascular Ultrasound, probe in a vessel) can alternatively be used.

The spherical distal tip 14 reflects the sonic energy more diffusely than a non-spherical tip, to provide an ultrasonic image of the distal end of the catheter from a wide range of angles relative to the viewing direction of the ultrasonic imaging device. Additionally, the spherical distal tip 14 formed of a polymeric and metallic materials uses less metal in the distal tip than a solid metal distal tip or band electrode, and the metallic portions are in contact with the sonic energy damping plastic material 33, so that the tip pyramid artifact has a desired low level of brightness and shorter duration or is absent entirely from the display.

In one embodiment, during ultrasonic imaging of the catheter 10, one or more of the lumens of the catheter shaft are filled with an aqueous fluid so that a plastic-aqueous fluid interface is formed which reflects less sonic energy than a plastic-air interface. Specifically, the ultrasonic image is produced with the aqueous fluid within the needle lumen 15 of the shaft. In embodiments having one or more additional lumens, in addition to the needle lumen 15 of the shaft, the one or more additional lumens are preferably also filled with the aqueous fluid during ultrasonic imaging. For example, the lumenal space, if any, of the tubular body member 21, between the inner surface of the tubular body member 21 and the outer surface of the inner tubular members 25, 26, is preferably filled with the aqueous fluid during ultrasonic imaging.

In a presently preferred embodiment, the catheter 10 has an impedance matching outer jacket layer 50 on an outer surface of at least a portion of the shaft 11, configured to decrease the reflected wave ultrasonic signal of the catheter. The impedance matching outer jacket layer 50 typically extends along at least a portion of the distal section of the shaft, and preferably is not provided on the proximal section 51. In the illustrated embodiment, the layer 50 has a distal end located proximal to the conical portion 31 and the spherical portion 30 of the spherical distal tip 14. The layer 50 is formed of a polymeric material, which in one embodiment is selected from the group consisting of a low density polyethylene (LDPE), EVA, or elastomers including neoprenes, silicones, SBS's (linear styrene-butadiene-styrene triblock copolymers, SB's (Radial styrene-butadiene block copolymers), SIS's (linear styrene-isoprene-styrene triblock copolymers), butadienes and polyurethanes. In an embodiment in which the layer 50 is formed of an elastomer such as polyurethane, a lubricious surface coating (not shown) is typically provided on an outer surface of layer 50 to decrease the relatively high friction of the elastomer. Although not illustrated, the outer jacket layer 50 preferably has an irregular wall thickness forming a rough outer surface.

In the embodiment illustrated in FIGS. 1 and 5, the outer jacket layer 50 is on an outer surface of the compression cage 22, with a proximal end bonded to a distal end of the multi-layered braid reinforced body of the proximal shaft section. In one embodiment, the layer 50 is fusion bonded to an underlying polymeric layer (not shown) formed of a compatible polymer. For example, in one embodiment, the layer 50 is formed of LDPE, and an underlying polymer layer forming part of the distal section 52 of the tubular member 21 is formed of a high or medium density polyethylene (HDPE, MDPE). However, the layer 50 can alternatively be friction fit onto the shaft, as for example in the embodiment in which the layer 50 is formed of an elastomeric material such as polyurethane, and the elastomeric layer 50 is applied by allowing a temporarily expanded the layer 50 to retract down onto the shaft 11.

The impedance matching outer jacket layer 50 has an acoustic impedance which is between an acoustic impedance of blood and an acoustic impedance of the adjacent layer of the section of the shaft underlying the outer jacket layer, such that it more closely matches the acoustic impedance of the blood than does the polymeric material forming the outer layer along the distal section 52 directly underneath the outer jacket layer 50. For instance, the acoustic impedance of blood is about $1.4 \times 10^5$ gram/(cm$^2$ sec), silicone is about $1.6 \times 10^5$ gram/(cm$^2$ sec), soft polyurethane is about $1.8 \times 10^5$ gram/(cm$^2$ sec), HDPE is about $2.2 \times 10^5$ gram/(cm$^2$ sec) and stainless steel is about $46 \times 10^5$ gram/(cm$^2$ sec). The large mismatch between the acoustic impedance of the material(s) forming the distal section 52 (i.e., in the absence of the layer 50), would cause a large proportion of the ultrasound wave to be reflected off the blood/catheter interface. The impedance matching outer jacket layer 50 is formed of a material which provides an intermediate impedance between blood and the material forming the distal section 52, so that at each material interface there is less mismatch, and more of the ultrasound wave propagates forward, rather than reflecting backward.

The impedance matching outer jacket layer 50 preferably has a thickness of a quarter or three quarter wavelength of the center frequency of the ultrasound waves emitted by the ultrasound imaging device or displayed by the ultrasonic imaging system, so that destructive interference occurs between the reflected waves from the outer and inner surfaces of the jacket layer 50. The acoustic properties (e.g. acoustic impedance) of the outer jacket layer 50 (and/or the inner portions of the distal catheter shaft 11) may be chosen or adjusted such that the amplitudes of the reflected waves from the outer and inner surfaces of the jacket layer 50 are more equal and thus destructively interfere to produce a lower amplitude resulting reflected echo. Such adjustments may be made according formulas relating acoustic impedance to acoustic reflection and relating the physical properties of materials and mixtures to their acoustic impedance, as are well known in the art. The quarter or three quarter wavelength, impedance matching outer jacket layer 50 facilitates producing an ultrasonic image of the catheter shaft 11 at the perpendicular (direct echo) viewing direction which is not disadvantageously bright, to minimize the catheter curved body artifact in 3D echo systems.

The thickness of the quarter or three quarter wavelength layer is determined based on the speed of sound in the polymeric material of the layer and the desired frequency setting of the ultrasonic imaging device. For example, in one embodiment, the quarter wavelength impedance matching layer 50 is selected from the group consisting of a polyethylene layer having a thickness of about 0.0049 inches, and a polyurethane layer having a thickness of about 0.0044 inches, for use with ultrasonic imaging at a center frequency of 4 MHz. It should be noted that the values given above are typical of LDPE and soft polyurethanes, however, there are many polyurethane and polyethylene formulations that have a different sound velocity properties.

Figures 9, 10, 11:
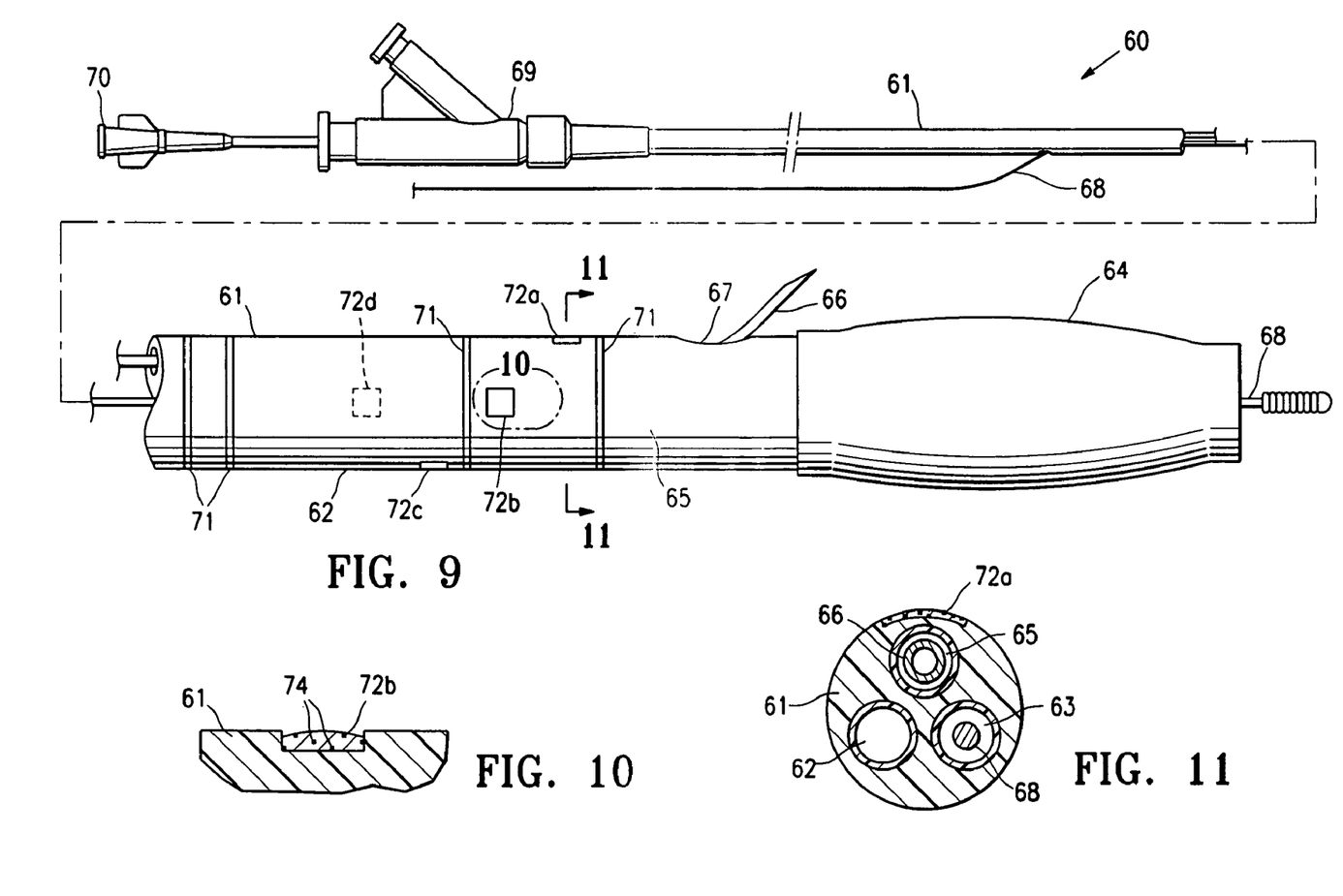
FIG. 9 is an elevational view of an alternative echogenic needle catheter embodying features of the invention, having rotational orientation echogenic portions on an outer surface of the catheter shaft.
FIG. 10 illustrates an enlarged, longitudinal cross sectional view of the catheter of FIG. 9, taken within circle-10.
FIG. 11 is a transverse cross sectional view of the catheter of FIG. 9, taken along line 11-11.

FIG. 9 illustrates an elevational view of an alternative needle catheter 60 embodying features of the invention, having rotational orientation markers. In the embodiment of FIG. 9, the transvascular needle catheter 60 generally comprises an elongated shaft 61 having a proximal section, a distal section, and a needle lumen 65 (see FIG. 11) in communication with a distal port 67 which is in a side wall of the distal shaft section and which is spaced proximally from the distal end of the catheter, and a needle 66 slidably disposed in the needle lumen. Although not illustrated, the shaft 61 typically has reinforcements, such as metallic braided reinforcing filaments embedded in the polymeric material of the wall of the shaft 61. FIG. 9 illustrates the needle in an extended configuration, extending out the port 67 away from the longitudinal axis of the catheter 60. A proximal adapter 69 on the proximal end of the shaft has a port 70 configured for providing access to the needle 66 for delivery of an agent, or for aspiration, through the lumen of the needle 66. A variety of operative connectors may be provided at the proximal adapter depending on the desired use of the catheter 60. The catheter 60 can have a variety of suitable shaft configurations and/or operative distal ends, as are conventionally known. For example, for details regarding suitable transvascular needle catheter designs suitable for use with embodiments of the invention, see U.S. Pat. Nos. 6,283,947; 6,692,466; 6,554,801; and 6,855,124, incorporated by reference herein in their entireties. For example, in one embodiment (not shown), a distal end portion of the needle lumen extends along a proximal tapered section of the inflated balloon such that the extended needle is directed away from the longitudinal axis of catheter shaft.

The catheter shaft 61 has marker bands 71 on at least the distal section 62, which in a presently preferred embodiment are formed of a material having echo reflective properties which are different (preferably more highly reflective) than the adjacent portions of the catheter shaft. For example, in one embodiment the marker bands 71 are formed of a metal or a polymer/metallic material mixture. The marker bands 71 may or may also not be visible under fluoroscopy.

A plurality of rotational orientation portions 72a-72d are on an outer surface of the catheter shaft 61, and are formed of a material having echo reflective properties which are different (preferably more highly reflective) than the adjacent portions of the catheter shaft. In a presently preferred embodiment, the rotational orientation echogenic portions 72 are formed of the same material as the marker bands 71, such as a metal (i.e. gold, tungsten, tungsten-iridium), a higher acoustic impedance polymer, or a metal filled polymer. Thus, portions 72 may, or alternatively may not, additionally be visible under fluoroscopy. In the embodiment shown in FIG. 10, illustrating an enlarged partial longitudinal cross section of the catheter of FIG. 9, taken within circle-10, the rotational orientation echogenic portions 72 are formed of a mixture of a polymeric material and a metallic material 74. The polymeric/metallic material mixture facilitates bonding the portions 72 to the outer surface of the polymeric shaft 61, as for example by adhesive or preferably by fusion bonding. Alternatively, portions 72 may consist of metal, and in one embodiment (not shown), portions 72 formed of metal are soldered or otherwise connected to a metallic braided reinforcement within the polymeric wall of the shaft 61 for secure attachment.

In a presently preferred embodiment, the portions 72a-d all have the same size, shape, and material composition configured to produce an echo (image) on the ultrasonic image of the catheter which is not overly bright. The relative thickness of the rotational orientation echogenic portions 72 may be somewhat exaggerated in the figures for ease of illustration, and is preferably selected to avoid disadvantageously increasing the profile of the catheter. The rotational orientation echogenic portions 72 typically have a thickness of about 0.001" to about 0.008" and a length/width of about 0.010" to about 0.040", and may project slightly above the outer surface of the shaft 61 or be wholly or partially recessed within the outer surface (e.g., jacket layer) of the shaft 61, and are preferably slightly recessed below the outer surface of the shaft.

In a presently preferred embodiment, the shaft has an outer polymeric jacket layer with holes in it in which the rotational orientation echogenic portions 72 are placed and bonded to the shaft, and the portions 72 are formed of a metal, a metal filled polymer, or a high acoustic impedance plastic, with a curved outer surface to provide a direct image at the desired range of probe angles relative to the catheter shaft. Such a configuration facilitates ultrasonic imaging of the shaft (due to the jacket), and determining proximal and distal locations from markers 71, and determining rotational orientation from markers 72 which are easily imaged when on the side of the catheter facing the imaging probe.

FIG. 11 illustrates a transverse cross sectional view of the catheter of FIG. 9, taken along line 11-11. In the illustrated embodiment, the shaft 61 has an inflation lumen 62 and a guidewire lumen 63 in addition to the needle lumen 65 of the shaft 61. In the illustrated embodiment, the catheter 60 is configured for rapid exchange, with a guidewire 68 slidably disposed in guidewire lumen 63 and through a guidewire proximal port spaced distally from the proximal end of the shaft. However, a variety of suitable catheter shaft designs can be used as are conventionally known. A balloon 64 on the catheter distal section has an interior in fluid communication with the inflation lumen 62 for inflating the balloon. The inflated balloon 64 can be configured for a variety of suitable functions including to facilitate positioning the needle distal port 67 of the shaft against the vessel wall, or to anchor the catheter within the vessel lumen, or to occlude the vessel lumen. However, a variety of suitable shaft configurations can be used including shafts which do not have balloon 64, inflation lumen 62, and/or guidewire lumen 63, or which have one or more addition lumens such as a fluid delivery lumen configured for delivery of fluid such as medication or contrast agent to the patient from a port in the shaft distal section. Similarly, in alternative embodiments, the shaft 61 includes one or more additional needle lumens with additional needles slidably disposed therein (not shown).

Under ultrasonic imaging, the distal most marker band 71 in the embodiment of FIG. 9 illustrates the longitudinal location of the needle port 67 of the shaft 61. However, because the marker bands 71 are uniform around the entire circumference of the catheter shaft 61, the ultrasonic image of the marker bands 71 will appear irrespective of the rotational orientation of the catheter. Practical injection needles 66 are generally too small to reflect sound waves well enough to be imaged by echo systems. Also, the needle 66 is often shielded from the sound waves by the catheter shaft 61. Thus, the needle 66 will not be seen/be distinguishable in the ultrasonic image.

The rotational orientation echogenic portions 72 are arranged in an array in which each adjacent pair of portions 72 are circumferentially and longitudinally spaced apart from one another. In the embodiment of FIG. 9, four portions 72a-d are proximally adjacent to the needle port 67, and are circumferentially spaced apart in 90° intervals around the circumference of the shaft. However, alternative numbers and spacings can be used depending on factors such as the desired orientation determination performance characteristics of the catheter, the echogenicity and orientation of the portions 72, and the catheter shaft design. In a presently preferred embodiment, at least 4 portions 72 are provided.

Figure 12:
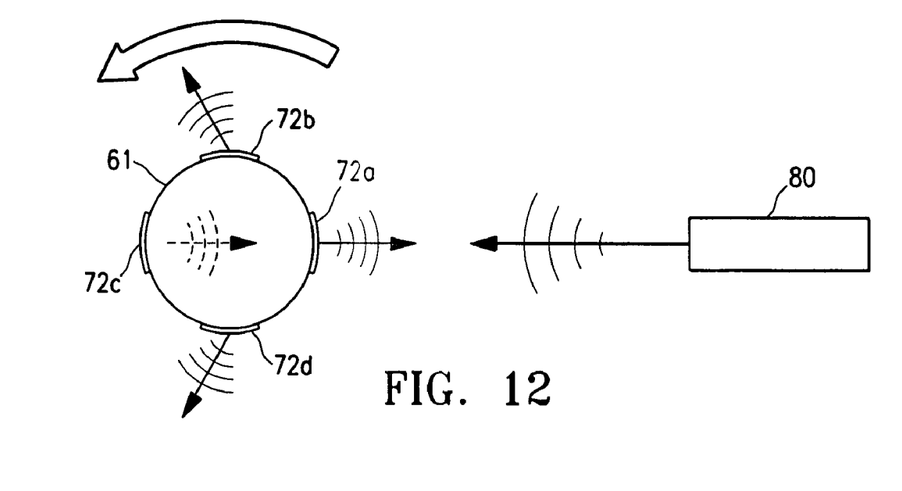
FIG. 12 illustrates the direct reflection of sound waves from an ultrasonic imaging probe relative to a transverse sectional perspective view of the catheter of FIG. 9 taken through portion 72a and looking proximally so that the proximally spaced portions 72b-d are also visible.

FIG. 12 shows a perspective transverse view of the catheter of FIG. 9, through portion 72a, and looking proximally so that the proximally spaced portions 72b-d are also visible, to illustrate the direct reflection of sound waves from an ultrasonic imaging probe 80. The portion 72a that is directly in the path of the sound wave and presents a face surface that can directly reflect an echo back to the probe 80, will be imaged the brightest. The portion 72c on the side of the catheter opposite to the ultrasonic imaging probe 80 will produce a direct reflection, but because the sound waves that hit it and its reflected echo must pass thru the catheter body, its echo will have a small amplitude and be displayed much less bright (or not at all) than the portion 72a (some of the sonic energy is reflected off the catheter body/blood interface and some of the sonic energy is dissipated as heat in the plastic catheter body). The two portions, 72b and 72d, which are 90 degrees from the portion 72a (i.e., the face surface of each portion 72b and 72d is oriented at 90 degrees from the path of the sound wave) will produce an echo directed away from the ultrasonic imaging device probe and will therefore not be imaged.

Figure 13:
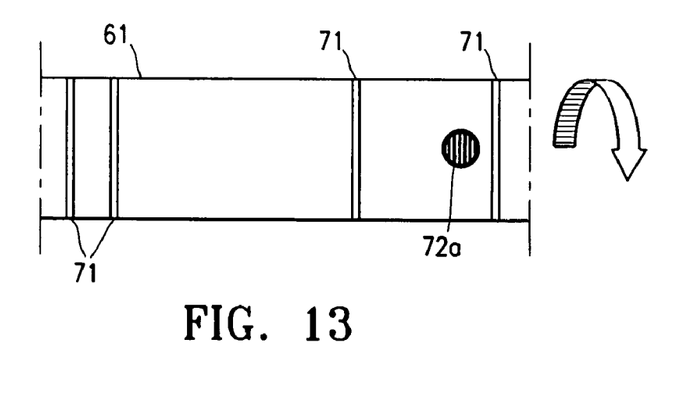
FIG. 13 is a representation of the displayed 3D ultrasonic image of a section of the catheter of FIG. 9 by an ultrasonic imaging device probe oriented relative to the catheter as shown in FIG. 12.
Figure 14:
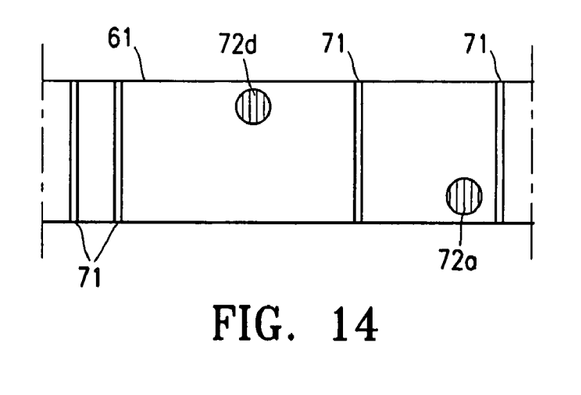
FIG. 14 is a representation of the displayed 3D ultrasonic image after rotation the catheter 45° in the direction of the arrow shown in FIGS. 12 and 13.

FIG. 13 is a representation of the displayed 3D ultrasonic image of a section of the catheter of FIG. 9 by the probe oriented as shown in FIG. 12. Only portion 72a with its most direct reflected echo shows up in a distinguishable manner in this representation. In alternative embodiments, the other portions 72b-d could be made distinguishable in the view of FIG. 13, but will be much less bright than portion 72a (e.g., using portions 72 formed of more highly echogenic materials/structural shapes, or different echo system display settings). FIG. 14 is a representation of what the same image in FIG. 13 would look like if the section of the catheter in FIG. 13 were rotated 45° in the direction shown by the arrow in FIGS. 12 and 13. In this case, both portions 72a and 72d are in the direct path of the probe's sound waves and are only 45° from the most direct reflection path shown in FIG. 12. Thus, they are equally bright, and brighter than portions 72b and 72c, but dimmer than portion 72a was in FIG. 13 (the brightness being represented in the figures by the degree of shading). In other embodiments, the outer surfaces of the portions 72 could be curved such that 72a and 72d were equally as bright as portion 72a was in FIG. 13.

At least at 45° intervals in the embodiment of FIG. 9, the rotational orientation of the catheter 60 relative to the probe 80 may be easily distinguished by distinctive echo images of this section of the catheter 60. Thus, the rotational orientation of the needle 66 (or any other feature locked to the catheter body) can be determined from the 3D echo image. Additionally, the distal end of this catheter section is distinguishable from its proximal end by the marker bands 71. Because the needle 66 is near the distal marker band 71, the location of the needle 66 in the ultrasonic image is known. It should also be evident that, when in the patient's body, a 3D image of the patient's body tissues would be present and thus, the location and direction of the needle travel would be known relative to the imaged anatomy. This is true in any projection, if the position/direction of the probe 80 is known or indicated on the image. Thus, the catheter 60 facilitates directing the needle 66 into the desired anatomy in the desired direction by observing a 3D image display, and manipulating the catheter (rotational and/or longitudinal manipulations) as needed. It should also be evident that many modifications can be made to distinguish other rotational orientation intervals or other catheter features. The number and location of the rotational orientation echogenic portions 72 and the number and positions of marker bands 71 are selected to preferably provide incremental information regarding the rotational orientation of the catheter and the proximal and distal ends of the orientation indicating section of the catheter shaft. Thus, a small amount of rotation produces a distinguishable change in the ultrasonic image of the array of portions 72, providing highly detailed information about the catheter rotation. For example, the array of portions 72 of the embodiment of FIG. 9 would produce a different image depending on whether the catheter was rotated 45° clockwise or counterclockwise. Additionally, due to the number and spacing of the rotational orientation echogenic portions 72 in the embodiment of FIG. 9, the catheter 60 does not have to be rotated to determine the rotational orientation of the catheter in the patient's body, because one or more of the portions 72 will be visible in an ultrasonic image of the catheter.

In one embodiment, a method of the invention includes overlaying or alternating a 3-D echo image of a needle catheter of the invention with an image (such as a 3-D echo, 3-D biplanar fluoro or CT image) of the patient's blood vessels adjacent to the needle catheter. The blood vessel image is typically obtained using contrast injections into the arteries and/or veins. By overlaying or alternating the images, the method thus avoids injecting the needle into the adjacent blood vessels during a procedure using a transvascular or intraventricular needle catheter of the invention.

While the present invention is described herein in terms of certain preferred embodiments, those skilled in the art will recognize that various modifications and improvements may be made to the invention without departing from the scope thereof. For example, the damping features of the distal tip electrode may be used to reduce the ultrasonic imaging artifacts of other elements such as other electrodes or markers on the catheter. Additionally, while discussed primarily in terms of a needle catheter, it should be understood that a variety of medical devices can be used which embody features of the invention including surgical and implantable devices, and other catheters such as balloon catheters, guiding catheters, ablation catheters, device delivery catheters and catheters that accommodate or incorporate sensors (i.e. temperature, chemical, oxygen, etc.). For example, the needle can be eliminated and solution infused through the empty lumen of the catheter (e.g., to inject directly into the bloodstream just proximal of the area to be treated). Additionally, in vessel injection systems, the spherical tip will likely not need to function as an electrode, so the conduction requirement may be omitted.

Thus, the echogenic catheter features being disclosed are applicable to all types of catheters/other devices that may be guided by ultrasound and/or must be present in the anatomy during ultrasonic imaging. Additionally, although the catheter features are useful for use with 2D or 3D ultrasonic imaging systems, it should be noted that for the purpose of catheter guidance, a 3D echo system is preferred to the "slice" image provided by a 2D echo system. A 2D echo system produces images that are like viewing a very thin planar slice thru the anatomy and the catheter, making it extremely difficult to distinguish/find a catheter, follow a catheter to its tip or other relevant portion and determine where in the anatomy the relevant portion of a catheter is located/oriented or is located/oriented relative to a previous location/orientation. A 3D echo system produces images that can either be a see-through representation of large 3D volume of the anatomy and catheter or a 3D surface image of the same. In a 3D image, anatomic reference points abound in the image and, with a properly echogenic catheter (as described in this application), all portions of the catheter in the image volume may be seen, and the direction of the catheter shaft relative to the anatomy is easily visualized as described herein.

Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An echogenic needle catheter, comprising:
   a) an elongated shaft having a proximal end, a distal end, and a needle lumen;
   b) a spherical distal tip at the distal end of the elongated shaft, having an outer surface with a circumference angle substantially greater than 180 degrees, having a rigid outer diameter wall with a curved outer surface formed at least in part of a rigid polymeric material, and having a lumen in communication with a proximal section of the needle lumen of the shaft and with a port at a distal end of the spherical distal tip, wherein the spherical distal tip is formed at least in part of an electrically conductive material, and the spherical distal tip is in continuous contact with the lumen;
   c) a needle in the needle lumen of the shaft, which extends distally from the spherical distal tip port in an extended configuration, and which has a lumen; and
   d) a conductor electrically connected to the spherical distal tip and extending through the shaft to the proximal end, so that the spherical distal tip is an electrode, the conductor including an elongated deflection member with a distal end secured to the shaft, configured for deflecting a distal section of the catheter shaft.

2. The needle catheter of claim 1 wherein the wall is a nonconductive polymer and the tip further includes a metallic pin member within the polymeric wall, the pin member having an exposed distal end distal to the polymeric wall.

3. The needle catheter of claim 2 wherein the metallic pin member is electrically connected to a conductor, so that the spherical distal tip is an electrode.

4. The needle catheter of claim 1 wherein the wall has an outer layer defining an outer surface of the spherical distal tip formed of a metallic material.

5. The needle catheter of claim 1 wherein the wall defines an outer surface of the spherical distal tip and comprises a mixture of a polymer and a metallic material.

6. The needle catheter of claim 1 wherein the needle has a retracted configuration in which a distal end of the needle is within the spherical distal tip lumen.

7. The needle catheter of claim 1 wherein the spherical distal tip has a spherical distal portion and a conical tip support proximal portion with an outer surface tapering distally.

8. The needle catheter of claim 1 including a second electrode on a proximal shaft section.

9. The needle catheter of claim 1 wherein the elongated shaft has a quarter or three quarter wavelength impedance matching outer jacket layer extending along at least a portion of a distal section of the shaft proximal to at least a section of the spherical distal tip, the outer jacket comprising a polymeric material with an acoustic impedance which is between an acoustic impedance of blood and an acoustic impedance of the adjacent layer of the section of the shaft underlying the outer jacket layer, such that it more closely matches the acoustic impedance of blood than does the adjacent layer of the section of the shaft underlying the outer jacket layer, so that the outer jacket is configured to decrease the reflected wave ultrasonic signal of the catheter.

10. The needle catheter of claim 9 wherein the outer jacket layer polymeric material is selected from the group consisting of a low density polyethylene, and an elastomer, and the outer jacket layer has an irregular wall thickness forming a rough outer surface.

11. The needle catheter of claim 1, wherein the deflection member includes a proximal end connected to a proximal adapter, and wherein the deflection member extends within a lumen between the proximal adapter and the distal end of the deflection member.

12. The needle catheter of claim 11, wherein the deflection member is connected to a pin disposed in the spherical distal tip, the pin forming the electrode.

13. The needle catheter of claim 1, wherein the spherical distal tip comprises a first material forming a solid shape between the ridged outer diameter wall and an inner surface of the first material that is touching and in continuous contact along an outer surface of a metallic pin member within the spherical distal tip.

14. The needle catheter of claim 1, wherein the spherical distal tip comprises a first material forming a solid shape between the ridged outer diameter wall and an inner surface of the first material that is touching and in continuous contact along an outer surface a metallic pin member within the spherical distal tip.

15. An echogenic needle catheter, comprising:
   a) an elongated shaft having a proximal end, a distal end, and a needle lumen;
   b) a spherical distal tip at the distal end of the elongated shaft, having an outer surface with a circumference angle substantially greater than 180 degrees, and having a lumen in communication with a proximal section of the needle lumen of the shaft and with a port at a distal end of the spherical distal tip, wherein the spherical distal tip is formed at least in part of an electrically conductive material, and the spherical distal tip is in continuous contact with the lumen;
   c) a needle in the needle lumen of the shaft, which extends distally from the spherical distal tip port in an extended configuration, and which has a lumen;
   d) a conductor electrically connected to the spherical distal tip, so that the spherical distal tip is an electrode; and
   e) a second electrode on a proximal shaft section, wherein the shaft comprises a proximal shaft section having a braided or coiled metal support layer, and the second electrode is electrically connected to the braided or coiled metal support layer.

16. The needle catheter of claim 1, wherein the spherical distal tip comprises a first material forming a solid shape between the ridged outer diameter wall and an inner surface of the first material that is touching and in continuous contact along an outer surface of a metallic pin member within the spherical distal tip.

17. An echogenic needle catheter, comprising:
   a) an elongated shaft having a proximal end, a distal end, and a needle lumen;
   b) a spherical distal tip at the distal end of the elongated shaft, having a lumen in communication with a proximal section of the needle lumen of the shaft and with a port at a distal end of the spherical distal tip, a rigid outer diameter wall with a curved outer surface formed at least in part of a rigid polymeric material, and a high strength support member which is within the spherical distal tip and extending proximally therefrom and which has a proximal end section secured to the distal end of the catheter shaft, wherein the spherical distal tip has a spherical distal portion with a rigid outer surface having an outer diameter greater than an outer diameter of the support member and a conical tip support proximal portion with an outer surface tapering distally towards the spherical distal portion, wherein the spherical distal tip is formed at least in part of an electrically conductive material, and the spherical distal tip is in continuous contact with the lumen; and
   c) a needle in the needle lumen, which extends distally from the spherical distal tip port in an extended configuration, and which has a lumen.

18. The needle catheter of claim 17 wherein the wall of the spherical distal tip is a nonconductive polymer, and the high strength support member is a metallic pin member within the polymeric wall, the pin member having an exposed distal end distal to the polymeric wall, and a proximal end section electrically connected to a conductor, so that the spherical distal tip is an electrode.

19. The needle catheter of claim 18 wherein the proximal end section of the metallic pin member has a grooved surface with a channel configured to receive the distal end of the conductor therein.

20. The echogenic medical device of claim 1, wherein the spherical distal tip comprises a first material forming a solid shape between the ridged outer diameter wall and an inner surface of the first material that is touching and in continuous contact along an outer surface of a metallic pin member within the spherical distal tip.

21. An echogenic medical device, comprising:
   a) a shaft having a proximal end, a distal end, and a lumen;
   b) a spherical distal tip at the distal end of the shaft, having an outer surface with a circumference angle substantially greater than 180 degrees, having a rigid outer diameter wall with a curved outer surface formed at least in part of a rigid polymeric material, and having a lumen in communication with a proximal section of the lumen of the shaft and with a port at a distal end of the spherical distal tip, wherein the spherical distal tip is formed at least in part of an electrically conductive material, and the spherical distal tip is in continuous contact with the lumen; and
   c) a conductor electrically connected to the spherical distal tip and extending through the shaft to the proximal end, so that the spherical distal tip is an electrode, the conductor including an elongated deflection member with a distal end secured to the shaft, configured for deflecting a distal section of the catheter shaft.

22. The echogenic medical device of claim 21, wherein the spherical distal tip comprises a first material forming a solid shape between the ridged outer diameter wall and an inner surface of the first material that is touching and in continuous contact along an outer surface of the pin.

* * * * *